United States Patent [19]

Bechthold et al.

[11] 4,399,689
[45] Aug. 23, 1983

[54] TEMPERATURE-CONTROLLED SAMPLE CELL FOR PHOTOACOUSTIC SPECTROSCOPY

[75] Inventors: Paul S. Bechthold, Pulheim-Dansweiler; Johann Chatzipetros, Frechen, both of Fed. Rep. of Germany

[73] Assignee: Kernforschungsanlage Jülich GmbH, Jülich, Fed. Rep. of Germany

[21] Appl. No.: 240,544

[22] Filed: Mar. 4, 1981

[30] Foreign Application Priority Data

Mar. 6, 1980 [DE] Fed. Rep. of Germany ....... 3008546

[51] Int. Cl.³ ............................................ G01N 29/00
[52] U.S. Cl. ......................................... 73/24; 73/579
[58] Field of Search .................................... 73/24, 579

[56] References Cited

U.S. PATENT DOCUMENTS

| 3,938,365 | 2/1976 | Dewey | 73/24 |
| 4,028,932 | 6/1977 | Rosencwalg | 73/24 |
| 4,163,382 | 8/1979 | Amer | 73/24 |

Primary Examiner—Anthony V. Ciarlante
Attorney, Agent, or Firm—Karl F. Ross; Herbert Dubno

[57] ABSTRACT

A cell for photoacoustic spectroscopy has a metal heat conductive rod immersed at one end in a liquid coolant and another end forming part of the sample-receiving cell for accurate control of the temperature to eliminate thermal distortion of the measurements.

11 Claims, 7 Drawing Figures

TEMPERATURE-CONTROLLED SAMPLE CELL FOR PHOTOACOUSTIC SPECTROSCOPY

FIELD OF THE INVENTION

Our present invention relates to a sample-receiving cell for photoacoustic spectroscopy and, more particularly, to a temperature-controlled and particularly a low-temperature cell for a photoacoustic spectrometer of the type in which a sample chamber is connected by a tube with a microphone chamber containing an acoustoelectric transducer, e.g. a detector microphone.

BACKGROUND OF THE INVENTION

The photoacoustic technique is based upon the work of A. G. Bell c. 1880 which resulted in the discovery that substances which are periodically illuminated by light can emit an acoustic or sound signal.

More modern work with this principle has resulted in the development of photoacoustic spectroscopy (see < > in *Optoacoustic Spectroscopy and Detection*, Yo Han Pao (Ed.) < A. Rosencwaig >, Academic Press, NY 1977) and the development since then of commercial apparatus for carrying out optoacoustic or photoacoustic spectroscopy.

In this technique, the sample is placed in a hermetically sealed cell connected to a microphone by an acoustic coupling medium such as a carrier gas filling the space between the sample and the microphone and forming a sound-transmitting medium.

The sample is irradiated with modulated light with modulation frequencies ranging from several Hz to several kHz.

The light absorbed by the sample produces heat which spreads in the sample as heat waves reaching the sample surface where these waves are transformed to compression and rarefaction waves of the adjacent thin layer of carrier gas.

Because of the periodic nature of the light beam directed at the sample and generated by a chopper, the heat waves are generated at a corresponding frequency and the alternating periodic heating of the gas layer at the sample surface results in pressure fluctuations which constitute alternating cycles of condensation and rarefaction, i.e. sound signals which are picked up by the microphone.

The amplified microphone signal is fed to a phase-sensitive lock-in amplifier and the reference frequency of the lock-in amplifier is made identical to the modulation frequency of the light source. The signal output can be plotted as a photoacoustic signal spectrum in which, for instance, the photoacoustic signal amplitude is plotted as the ordinate against the light frequency or wavelength along the abscissa.

The resulting photoacoustic spectrum is an indication of the absorption and thermodynamic characteristics of the sample material.

Photoacoustic spectroscopy can be used in chemistry, physics, biology and medicine and indeed wherever determinations of properties of materials must be made.

Generally the measurements are carried out at room temperature although cooled samples and especially measurements at cryogenic temperatures have been employed.

In the latter case, the sample-receiving vessel has been immersed in a bath of liquid nitrogen.

The boiling of the liquid cryogen, e.g. the liquid nitrogen, has been found to generate measurement distortions (perturbations and noise) which affect the results obtained and the accuracy of the measurements.

OBJECTS OF THE INVENTION

It is the principal object of the present invention to provide an improved sample cell for photoacoustic spectroscopy which avoids the problems of earlier cells as described.

Another object of this invention is to provide a measuring cell for photoacoustic spectroscopy which can be temperature controlled with improved precision but without the introduction of noise, perturbations and measurement distortions heretofore characterizing the use of low-temperature fluids for cooling purposes.

SUMMARY OF THE INVENTION

These objects and others which will become apparent hereinafter are attained, in accordance with the present invention, by providing the sample-receiving chamber of the measuring cell at least in part within a metal heat conductive rod or bar, one end of which is immersed in a liquid cryogen, e.g. liquid nitrogen, serving to cool the cell. The sample chamber, surrounded by a vacuum jacket, is thus formed in a temperature-controlled massive heat conductive body and can be connected with the microphone chamber through a thin-wall small cross section tube, preferably looped or bent, to maximize acoustic coupling while minimizing heat transfer from the sample chamber to the microphone chamber. The tube opens into the microphone chamber above an outlet of the sample chamber.

With the cell of the present invention, the distortions in the output signal due to boiling coolant are almost excluded since the boiling coolant is remote from the microphone chamber and the sample, the heat abstraction from the region of the sample being effected by the highly efficient conduction of the body or rod.

The acoustic signal is transmitted to the microphone chamber, which can be at room temperature, with a minimum of temperature change because of the small-cross section acoustic coupling tube which because of its looped or bent configuration can compensate for thermal contraction and expansion changes of the conductive rod.

Because the acoustic coupling tube opens into the microphone chamber above its communication point with the sample chamber, convective distortions are excluded as well.

According to a feature of the invention, the heat conductive rod is formed with an angle, i.e. the end which is immersed in the liquid cryogen may be formed on a portion of the rod which extends vertically while the sample chamber is formed on a horizontal portion of the rod, the two portions being interconnected detachably at the bend or angle.

The portion of the rod formed with the sample chamber is advantageously formed with a flange which can be connected to the flange of a heat conductive chamber-forming body and these two flanged portions may be provided with mating formations providing effective contact between them for maximum heat conductivity across the junction. The flange connection allows the chamber-forming body to be removed.

Since measurements over a wide range of temperatures require that the heat conductive body be associated with both heating and cooling means, it has been found to be advantageous to carry out the cooling in the manner described, i.e. by having the vertically extending portion of the heat conductive rod run into a Dewar flask containing the liquid nitrogen while the chamber-forming portion of the heat conductive rod is provided with a heating coil.

In practice, temperature control can be effected by the use of two heating filaments one of which at the flanged chamber forming part and the other at the neighboring end of the rod, e.g. separate coax heat conductors operating upon a copper rod enabled the temperature to be held constant with a tolerance of better than 0.1° K. The temperature measurement can be effected via thermoelements such as thermistors, thermocouples or platinum resistors.

The vacuum jacket serves to provide heat insulation for the sample chamber and the heat conductive rod and is especially required at the sample chamber end of the device to avoid the condensation which might occur on the chamber windows.

The vacuum jacket can be provided with windows which lie opposite the windows of the sample chamber which can be formed by a transverse bore in the end of the flanged body so that by providing these windows inwardly of the ends of the bore, a sample chamber can be obtained which is of especially small volume, e.g. less than 1 cm$^3$.

Since the photoacoustic signal increases as the volume of the carrier gas decreases, i.e. is inversely proportional to this volume, a minimum cell volume is desirable.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 5:
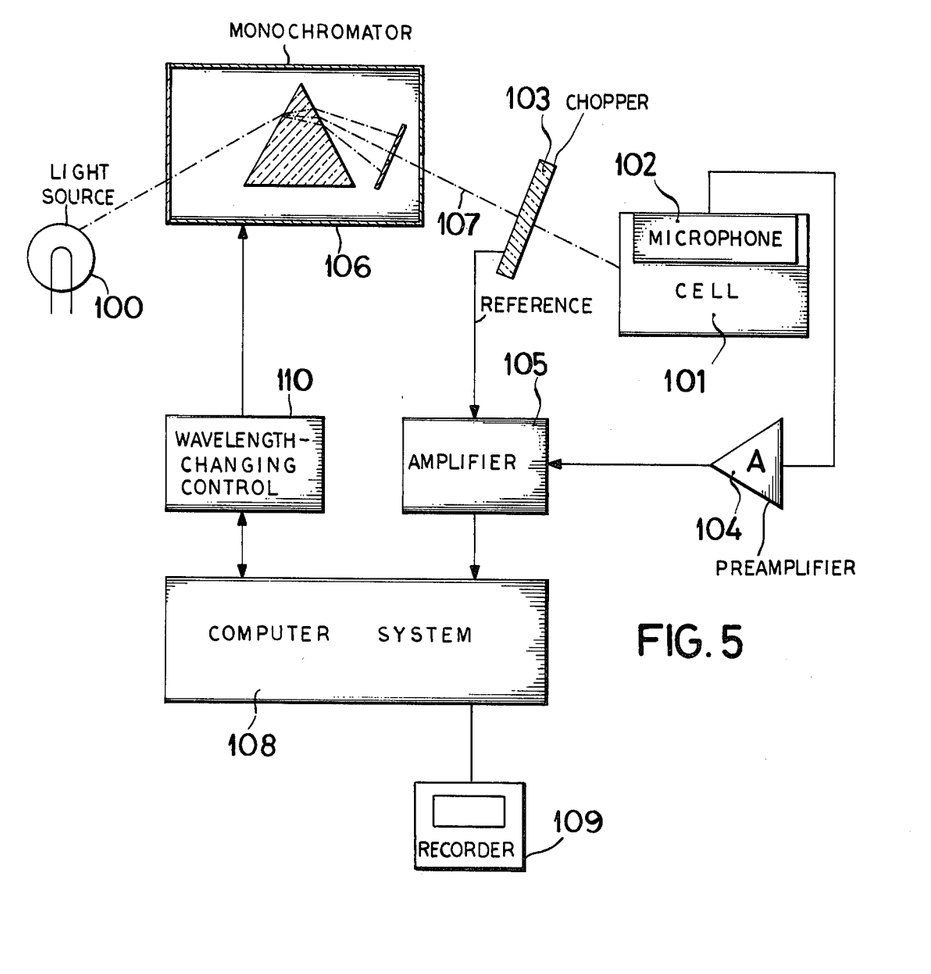
FIG. 5 is a diagram of a photoacoustic spectrometer for use with the cell of FIGS. 1 through 4.

Referring first to FIG. 5, it will be seen that a photoacoustic spectrometer can comprise a light source 100 directing a beam of light to a monochromator 106 which trains a collimated beam 107 through a chopper 103 into a sample in a photoacoustic cell 101 provided with a microphone 102 which can be at room temperature. The acoustic output is passed through a preamplifier 104 and then to a lock-in amplifier 105 tied to the frequency of the chopper 103, the output from the lock-in amplifier 105 being applied to a computer system for recordal and evaluation of the signal which produces the spectrogram of FIG. 6. The computer 108 thus is coupled to the recorder 109.

Figure 6:
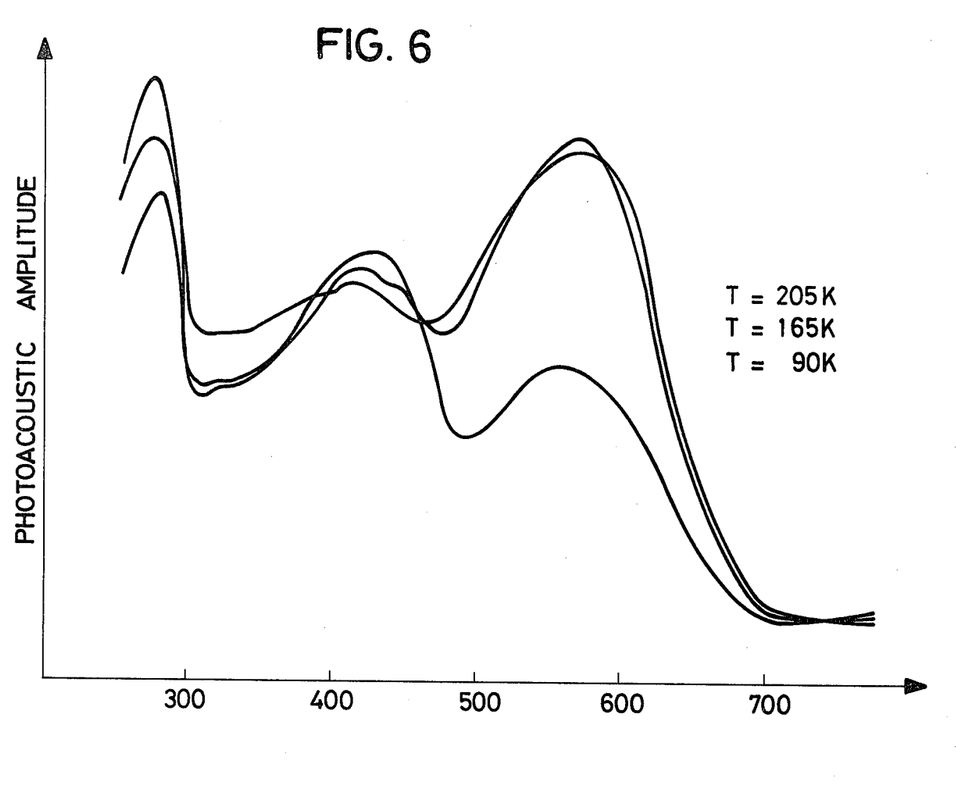
FIG. 6 is a spectrum obtained with this apparatus.

The frequency scan is effected by a controller 110 establishing the wave length at the monochromator as well. In FIG. 6, for a given material, measurements of the photoacoustic amplitude are plotted along the ordinate against wave length in nanometers along the abscissa, the photoacoustic spectrograms being given for temperatures of 205° K., 165° K. and 90° K. as indicated.

Figure 1:
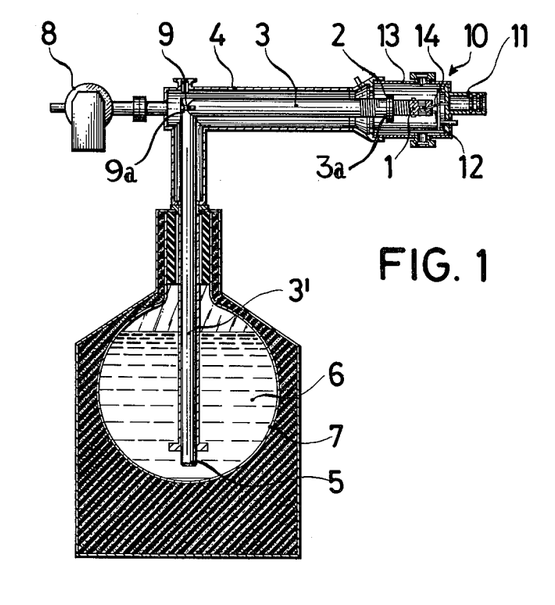
FIG. 1 is an axial cross-sectional view, partly in diagrammatic form of a cell embodying the invention.

The photoacoustic cell which can be used in the system of FIG. 5 and has the improved configuration of the present invention has been shown in FIG. 1 to comprise a sample chamber 1 within a temperature-controlled measuring cell and formed as a bore 1a in a massive metal body 2 of high thermal conductivity, e.g. aluminum or copper, with an inner aluminum surface.

The body 2 has a cylindrical portion 2a formed with helical grooves 2b in which heating coils can be fitted and terminates at one end in a transverse flange 2c surrounding a conical point or tip which fits into a complementary recess in a rod portion 3 of the same material so that the body 2 can be connected to the flange 3a of this rod portion by screws 3b. The rod portion 3 is connected at right angles to a rod portion 3', the members 2, 3, 3' forming a massive heat conductive body surrounded by a vacuum jacket 4 and having a free end 5 immersed in a coolant, e.g. liquid nitrogen, shown at 6 in a Dewar flask 7.

The vacuum jacket 4 is provided with a small ion getter pump to maintain the vacuum during the measurements (FIG. 1).

As is also apparent from this FIGURE, the vertical rod portion 3' is connected detachably to the horizontal portion 3 at a right bend 9 removably by a screw formed with complementary interfitting surfaces at this right angle joint.

The vacuum jacket 4 has an end portion 10 (FIG. 3) which is removable and can comprise a cylindrical sleeve 4a on a frustoconical transition piece 4b, an inwardly extending flange 4c being provided between these members.

Figure 3:
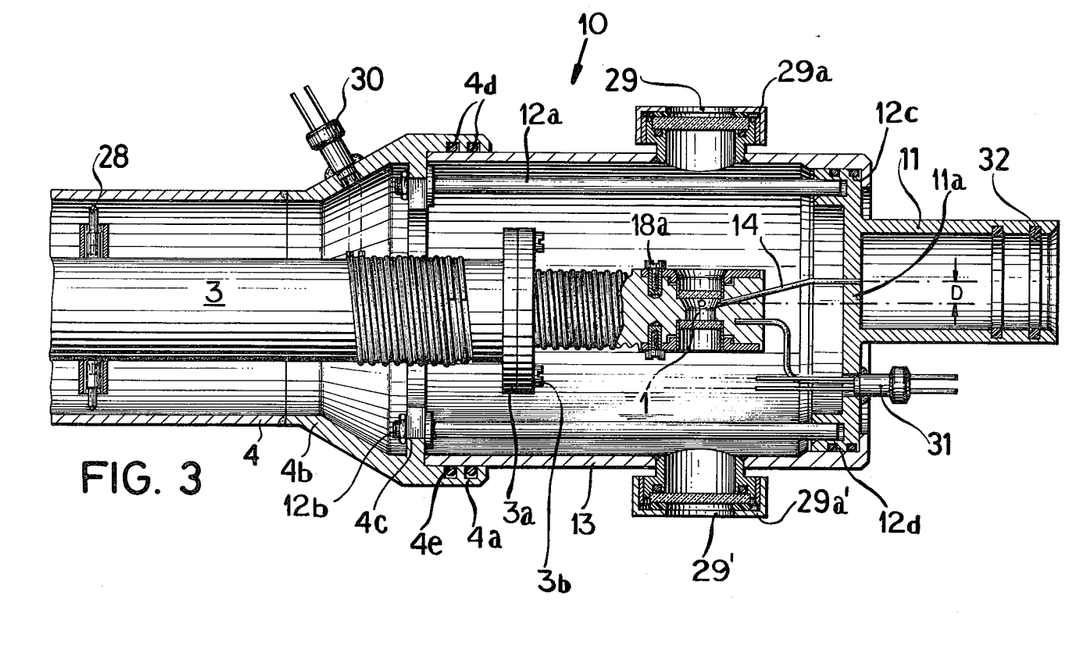
FIG. 3 is an axial section through the sample chamber end of the device.

The cylindrical portion 4a is provided internally with a pair of grooves 4d receiving respective O-rings 4e which seal around the exterior of the cylindrical member 13 of section 10.

The right-hand end (FIG. 3) of the sleeve 13 is closed by a cover 12 held in place by tierods 12a secured by nuts 12b to the flange 4c.

The cover 12 is provided with outwardly open peripheral grooves 12c receiving respective O-rings 12d which seal against the inner wall of the sleeve 13, the latter being removable when the vacuum is broken by pulling it off to the right.

The cover 12 is formed with a sleeve 11 adapted to define the microphone chamber and to receive a microphone at room temperature.

The sleeve 13 is provided with diametrically opposite windows 29.

The sample chamber 1 is connected with the microphone chamber through the bottom 11a of the microphone sleeve by a thin-wall small-diameter tube 14 which is bent and may even be looped (although it is shown in a simplified form in FIG. 3), to prevent transmission of expansion or contraction forces from the sample chamber and the body 2 to the microphone chamber.

This tube is of a length such that heat conduction therethrough to the microphone chamber is at a minimum although it affords optimum acoustic coupling and transfer of acoustic signals to the microphone chamber.

It is important that the tube 14 open into the microphone chamber at a point above the level of its outlet from the sample chamber. In FIG. 3, for example, the point at which the tube 14 opens into the microphone chamber is spaced by a distance D above the level at which this tube communicates with the sample chamber 1.

Figure 2:
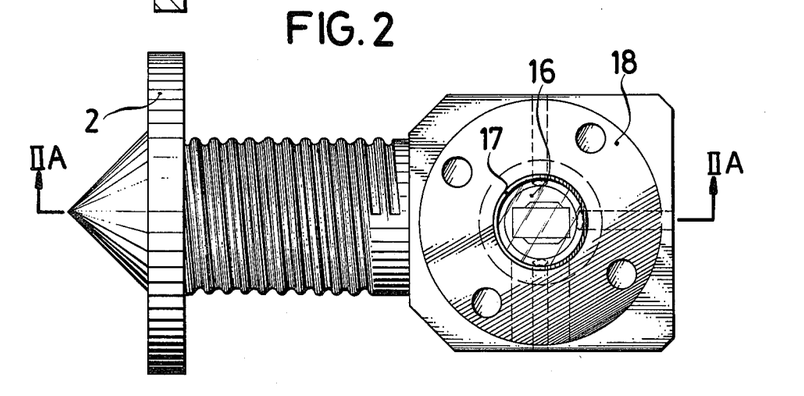
FIG. 2 is an elevation view of the sample chamber body.
Figure 2A:
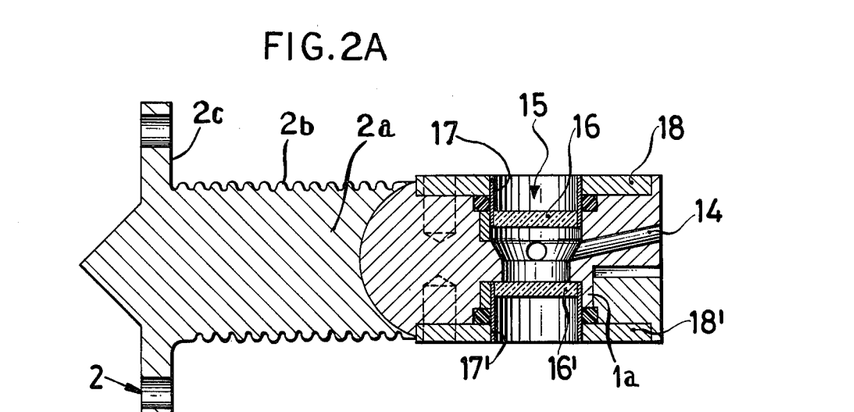
FIG. 2A is an axial section taken along the line IIA—IIA of FIG. 2.

The sample chamber 1, as can be seen more clearly from FIGS. 2 and 2A, is provided by a transverse bore in the enlarged end section 15 of the body 2 and is defined between windows 16, 16' of sapphire monocrystals set into the bore and held in place by epoxy resin in a thin vacon tube 17, 17' in a vacuum-tight manner. This tube is secured to a flange ring 18, 18' on the end section 15 by an indium ring sealing the flange against the sample chamber. The interior of the chamber is composed of aluminum.

Figure 4:
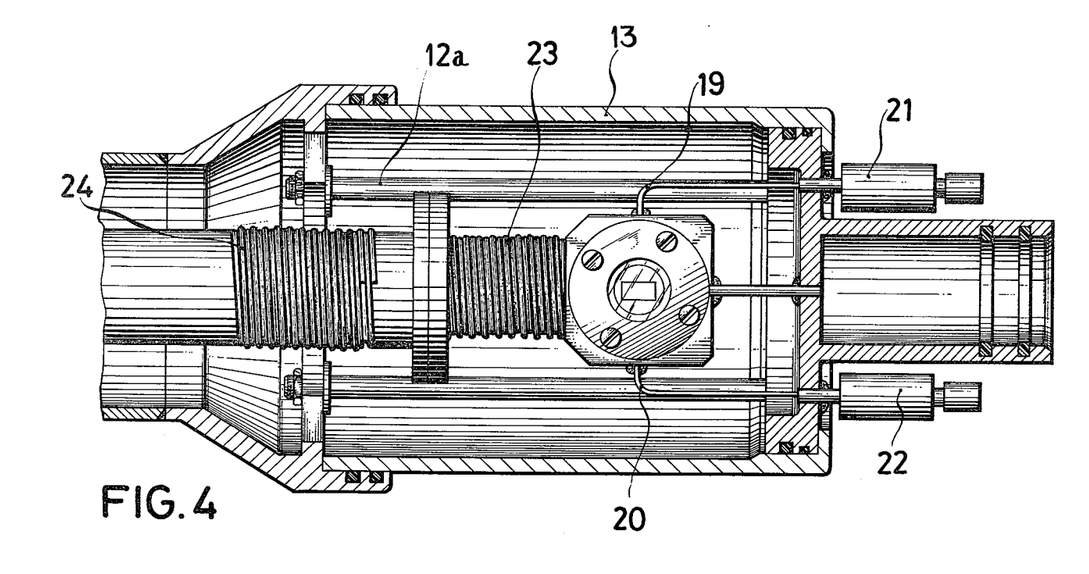
FIG. 4 is a section similar to FIG. 3 but taken in a direction at right angles to the direction of view in FIG. 3.

Further details of the chamber construction and the chamber-forming end of the bar will be apparent from FIGS. 3 and 4 which also show the end of the vacuum jacket in greater detail.

Thin connecting tubes 19 and 20 also communicate with the chamber 1 and via respective minicontrol valves 21 and 22, with a gas supply and the atmosphere respectively.

The minicontrol valve 21 is set to maintain the gas pressure in the cell constant and is so connected with the gas supply reservoir as to provide a minimum flow rate during each modulation period of the light source which is negligibly small although pressure equalization can be guaranteed over a large number of modulation fluctuations. The appropriate setting can be determined in the conventional manner by observing the microphone signal on an oscillograph. The valve 21 is then so throttled until the noise from the largest of the total volume of the cell and reservoir disappears. Valve 22, open to the atmosphere allows full replacement of the cell gas.

The heating coils 23 are provided on the body 2 and a further heating coil 24 can be provided at the chamber end of the rod portion 3. The heating coils can be connected to electric current connectors 30 and 31 shown in FIG. 3.

To enable removal of the measuring cell head, the sleeve 13 is initially withdrawn and then the bolts 12a are disconnected.

The head is then accessible and can be removed at the flange joint.

Radial pins 28 (FIG. 3) with pointed contacts center the rod portion 3 in the vacuum jacket.

The windows 29 and 29' are composed of quartz glass and are sealingly anchored in place by thread covers 29a and 29a' opposite the sapphire windows of chamber 1.

The microphone chamber can accommodate O-ring seals 32 which are put in place when the microphone is inserted into the sleeve 11 to rest against the bottom 11a thereof.

The measuring cell has the advantage that it requires a minimum of servicing and generates little noise during operation, especially almost excluding noise from the boiling of the coolant. The temperature of the sample is controllable and stable and the microphone may remain at room temperature.

The optical window of the cell has excellent transmissivity range and good thermal conduction characteristics, being readily dismounted for rapid sample changes. One need only remove the screws 18a holding one of the windows in place.

The cell volume can be less than 1 cm$^3$ so that a high signal level can be obtained and the gas pressure in the cell can be maintained constant the entire temperature range of measurements.

The spectrum which can be obtained using the cell of the present invention in the manner already described can utilize samples which are powders or frozen solutions which cannot be investigated adequately with conventional methods. The spectra which are obtained, of which FIG. 6 is an example, are particularly free from noise.

The spectra of FIG. 6 were taken of a frozen aqueous solution of the *purpur* membrane of *Halobacterium halobium*. The coolant loss in spite of the experiments run at higher temperatures was 10 l of nitrogen in three to four days and excellent temperature stability was observed.

We claim:

1. A temperature-controlled cell for photoacoustic spectroscopy comprising:
   an elongated massive heat conductive member having one end immersible in a coolant and formed at the opposite end with a measuring chamber for receiving a sample;
   means forming at least one window opening into said chamber for subjecting said sample to illumination;
   a vacuum jacket surrounding said member;
   a microphone chamber adapted to receive a microphone and communicating with said measuring chamber by a bend tube affording acoustic coupling of said measuring chamber with said microphone chamber while minimizing heat conduction therebetween, said tube opening into said microphone chamber at a level above the level at which it opens into said measuring chamber; and
   at least one heating coil on said opposite end of said member for varying the temperatures at which measurements are taken by said microphone of a sample in said chamber.

2. The cell defined in claim 1 wherein said member is a rod having two angularly adjoining portions including a substantially vertical portion formed with said one end and a substantially horizontal portion formed with said other end.

3. The cell defined in claim 2 wherein said measuring chamber is formed in a heat-conductive body forming said other end of said member and flanged removably to the other portion of said rod.

4. The cell defined in claim 3 wherein said other portion of said rod is formed with one heating coil and said body is formed with another heating coil.

5. The cell defined in claim 3 wherein said body and said other end of said rod are formed with mating conical formations at their junction.

6. The cell defined in claim 3 wherein said portions of said rod are detachably secured together at a right angle junction.

7. The cell defined in claim 3, further comprising a crown of pointed spacer elements positioning said horizontal portion of said rod in said jacket.

8. The cell defined in claim 1, further comprising means including a pair of minicontrol valves for regulating pressure and carrier gas exchange in said measuring chamber.

9. The cell defined in claim 1 wherein said windows are set into said bore to minimize the volume of said measuring chamber, said windows beinc composed of sapphire monocrystals.

10. The cell defined in claim 1, claim 3 or claim 6 wherein said jacket has a removable portion surrounding said other end of said member and said measuring chamber.

11. The cell defined in claim 10 wherein said removable portion of said jacket is provided with a cover at an end thereof formed with a sleeve receiving said microphone and defining said microphone chamber.

* * * * *